(12) United States Patent
O'Connor et al.

(10) Patent No.: US 10,702,381 B2
(45) Date of Patent: Jul. 7, 2020

(54) HEART VALVE REMODELING DEVICE

(71) Applicant: BOSTON SCIENTIFIC SCIMED, INC., Maple Grove, MN (US)

(72) Inventors: Tim O'Connor, Galway (IE); Pat O'Toole, County Galway (IE); Richard O'Sullivan, Turloughmore (IE); Marc Feeley, Mayo (IE); Paul Gunning, Roscommon (IE); Fergal Horgan, County Mayo (IE); Coley Smyth, County Clare (IE); Sean Shanley, County Galway (IE); Axel Linke, Markkleeberg (DE)

(73) Assignee: Boston Scientific Scimed, Inc., Maple Grove, MN (US)

(*) Notice: Subject to any disclaimer, the term of this patent is extended or adjusted under 35 U.S.C. 154(b) by 140 days.

(21) Appl. No.: 15/829,228

(22) Filed: Dec. 1, 2017

(65) Prior Publication Data

US 2018/0153688 A1    Jun. 7, 2018

Related U.S. Application Data

(60) Provisional application No. 62/428,734, filed on Dec. 1, 2016.

(51) Int. Cl.
*A61F 2/24* (2006.01)
*A61F 2/95* (2013.01)
*A61F 2/966* (2013.01)

(52) U.S. Cl.
CPC .......... *A61F 2/2418* (2013.01); *A61F 2/2436* (2013.01); *A61F 2/95* (2013.01);
(Continued)

(58) Field of Classification Search
CPC .......... A61F 2/95; A61F 2/243; A61F 2/2436; A61F 2/24; A61F 2/2412; A61F 2/2439;
(Continued)

(56) References Cited

U.S. PATENT DOCUMENTS 5,449,372 A    9/1995  Schmaltz et al.
7,749,245 B2   7/2010  Cohn et al.
(Continued)

FOREIGN PATENT DOCUMENTS

AU    2013270507 A1    1/2014
EP    2345380 A2       7/2011
(Continued)

OTHER PUBLICATIONS

"The Unballoon Non-Occlusive Modeling Catheter", LeMaitre Vascular, 73 pages, 2013.
(Continued)

*Primary Examiner* — Brian A Dukert
(74) *Attorney, Agent, or Firm* — Seager, Tufte & Wickhem LLP

(57) ABSTRACT

A heart valve remodeling device may include a delivery device including an inner shaft slidably disposed over a guidewire and an outer shaft slidably disposed over the inner shaft, and a braided stent fixedly attached to the inner shaft and the outer shaft. The braided stent may be translatable between an elongated configuration and a deployed configuration by movement of the inner shaft relative to the outer shaft. The braided stent may include a valve having two or more leaflets disposed within the braided stent. Adjacent leaflets of the two or more leaflets may form longitudinally-oriented commissures proximate a perimeter of the valve, the commissures being fixedly secured to the braided stent along their length.

18 Claims, 12 Drawing Sheets

(52) U.S. Cl.
CPC .......... *A61F 2002/9511* (2013.01); *A61F 2002/9665* (2013.01); *A61F 2220/0075* (2013.01); *A61F 2230/0069* (2013.01)

(58) Field of Classification Search
CPC ............ A61F 2/2427; A61F 2002/9511; A61F 2002/9505; A61F 2002/9655
See application file for complete search history.

(56) References Cited

U.S. PATENT DOCUMENTS

| | | |
|---|---|---|
| 8,579,962 B2 | 11/2013 | Salahieh et al. |
| 8,828,040 B2 | 9/2014 | Goff |
| 8,951,280 B2 | 2/2015 | Cohn et al. |
| 9,179,896 B2 | 11/2015 | Machold et al. |
| 9,339,230 B2 | 5/2016 | Kassab |
| 2003/0040772 A1 | 2/2003 | Hyodoh et al. |
| 2005/0015112 A1 | 1/2005 | Cohn et al. |
| 2005/0137686 A1* | 6/2005 | Salahieh ............... A61F 2/2418 623/2.11 |
| 2005/0203615 A1 | 9/2005 | Forster et al. |
| 2006/0074483 A1* | 4/2006 | Schrayer ............... A61F 2/2412 623/2.1 |
| 2009/0287290 A1 | 11/2009 | Macaulay et al. |
| 2010/0249921 A1 | 9/2010 | Cohn et al. |
| 2014/0296706 A1 | 10/2014 | Chronos et al. |
| 2014/0336506 A1 | 11/2014 | Goff |
| 2015/0142102 A1 | 5/2015 | Lafontaine et al. |
| 2015/0351908 A1 | 12/2015 | Keränen et al. |

FOREIGN PATENT DOCUMENTS

| | | |
|---|---|---|
| WO | 2004043293 A2 | 5/2004 |
| WO | 2011005877 A1 | 1/2011 |
| WO | 2013059697 A2 | 4/2013 |
| WO | 2013126779 A1 | 8/2013 |
| WO | 2015173794 A1 | 11/2015 |

OTHER PUBLICATIONS

"PCT/US2017/064230 International Search Report and Written Opinion" dated Apr. 6, 2018.

\* cited by examiner

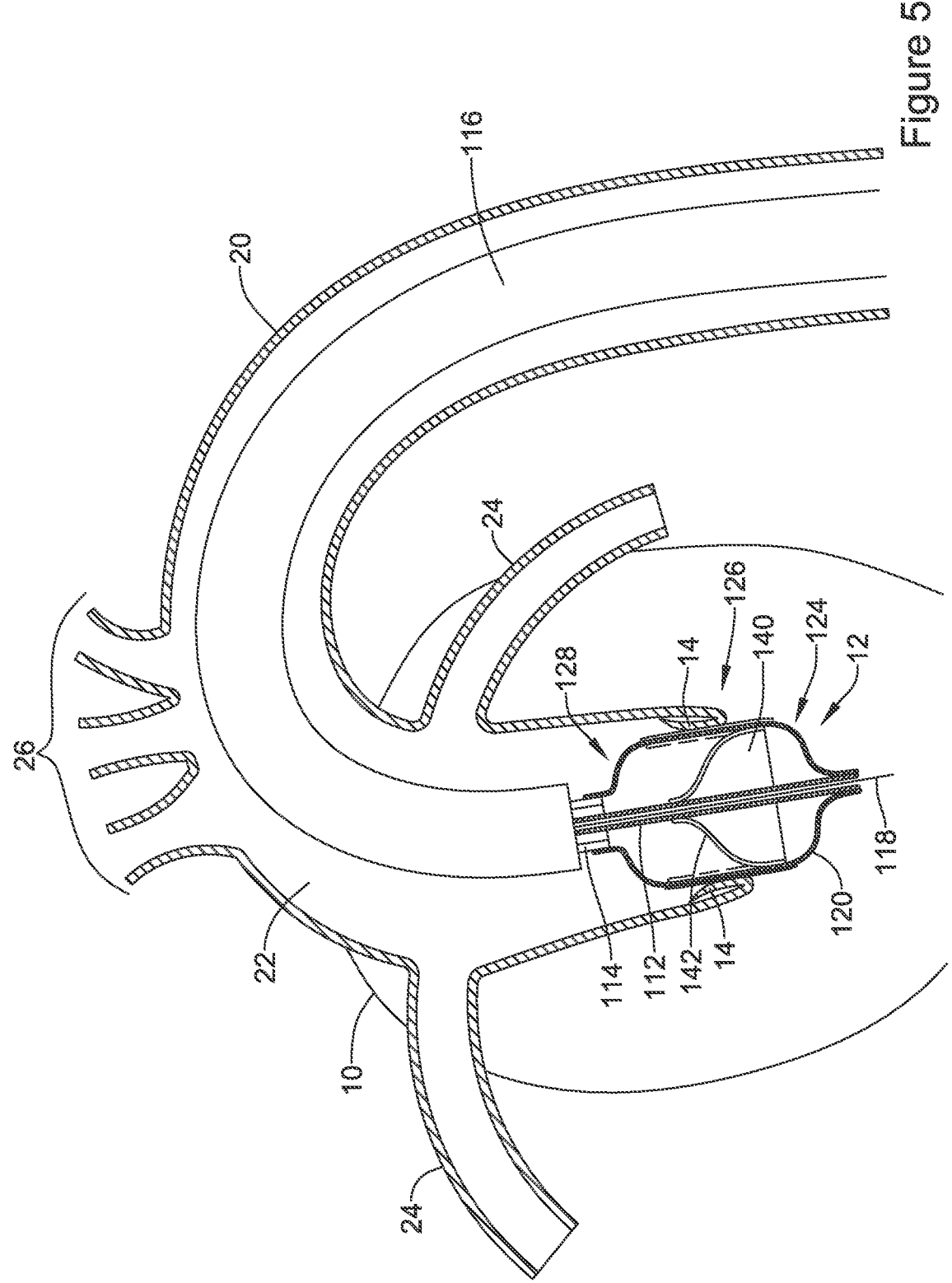

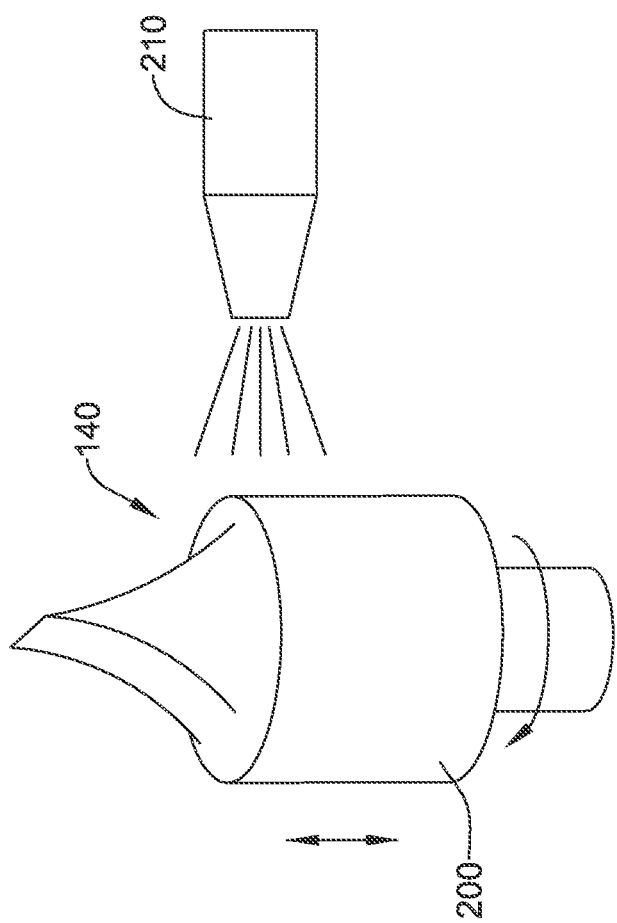

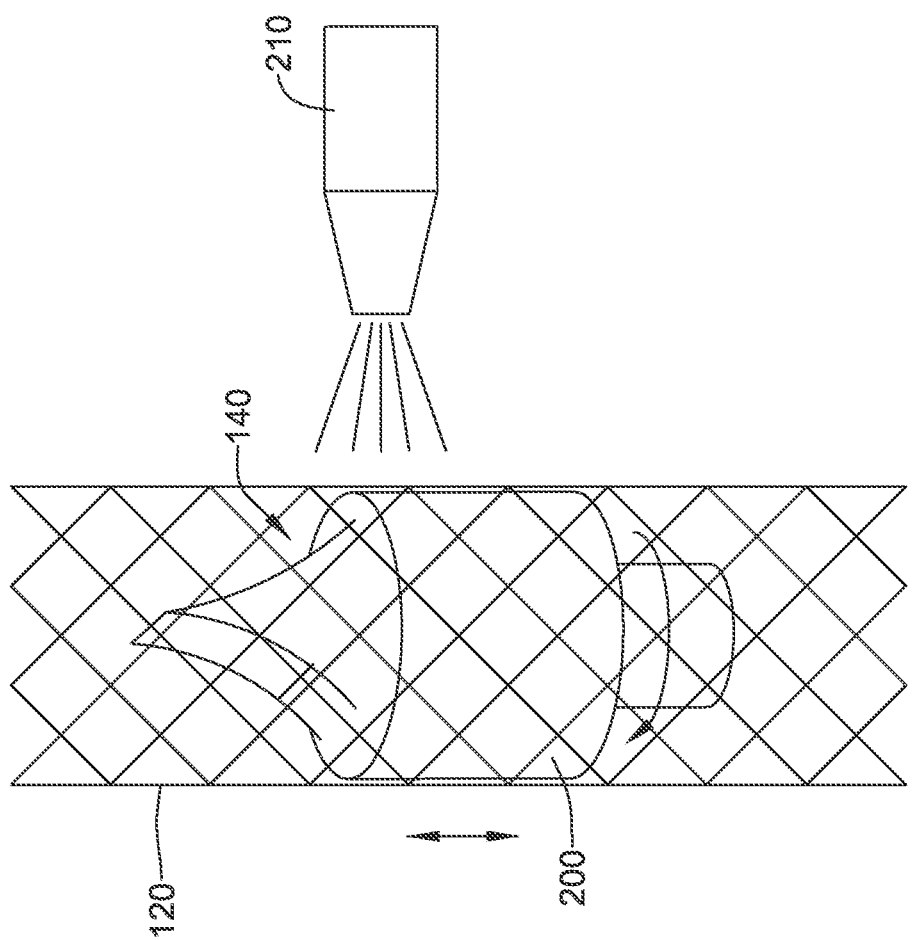

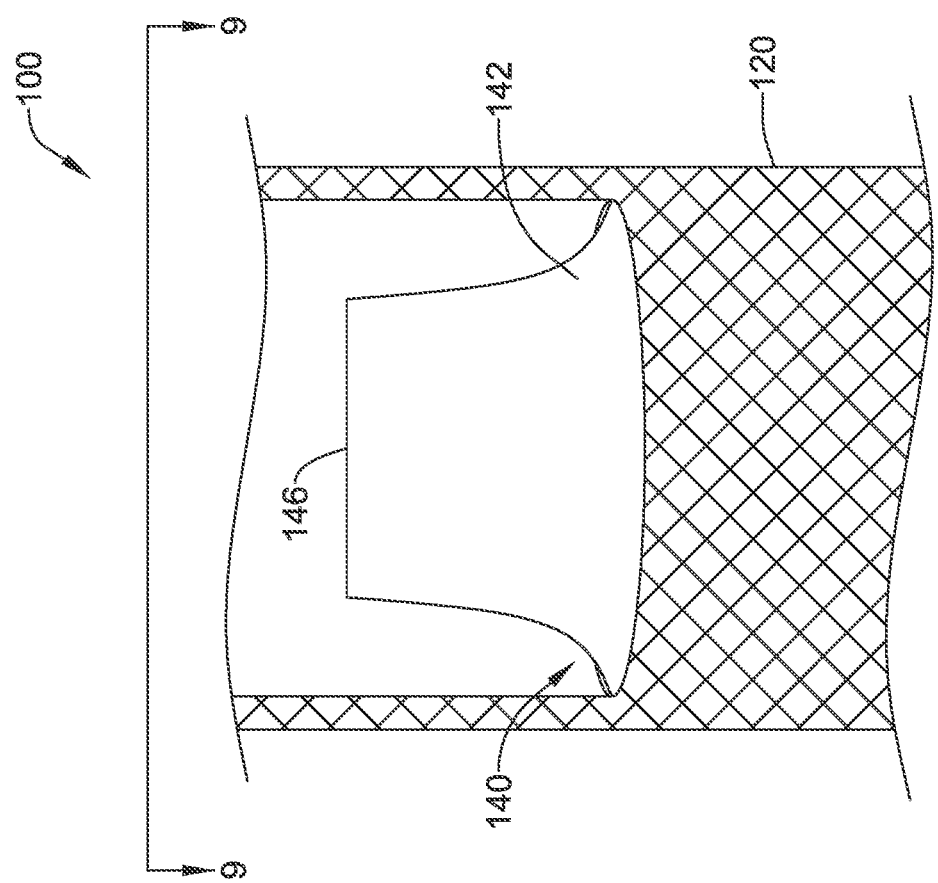

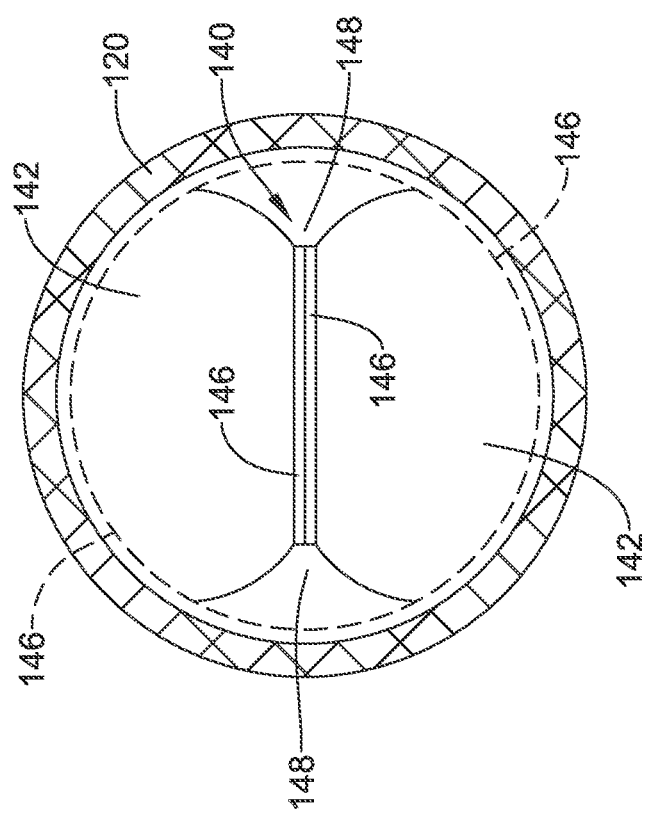

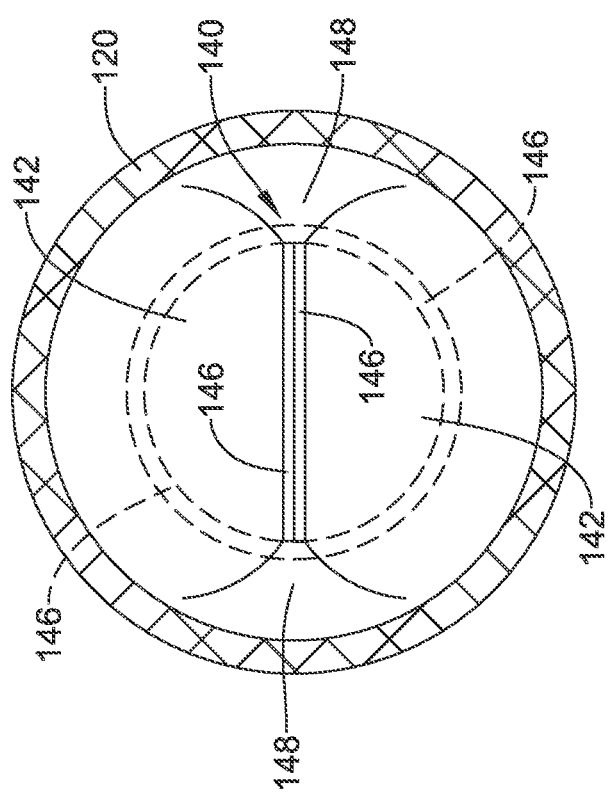

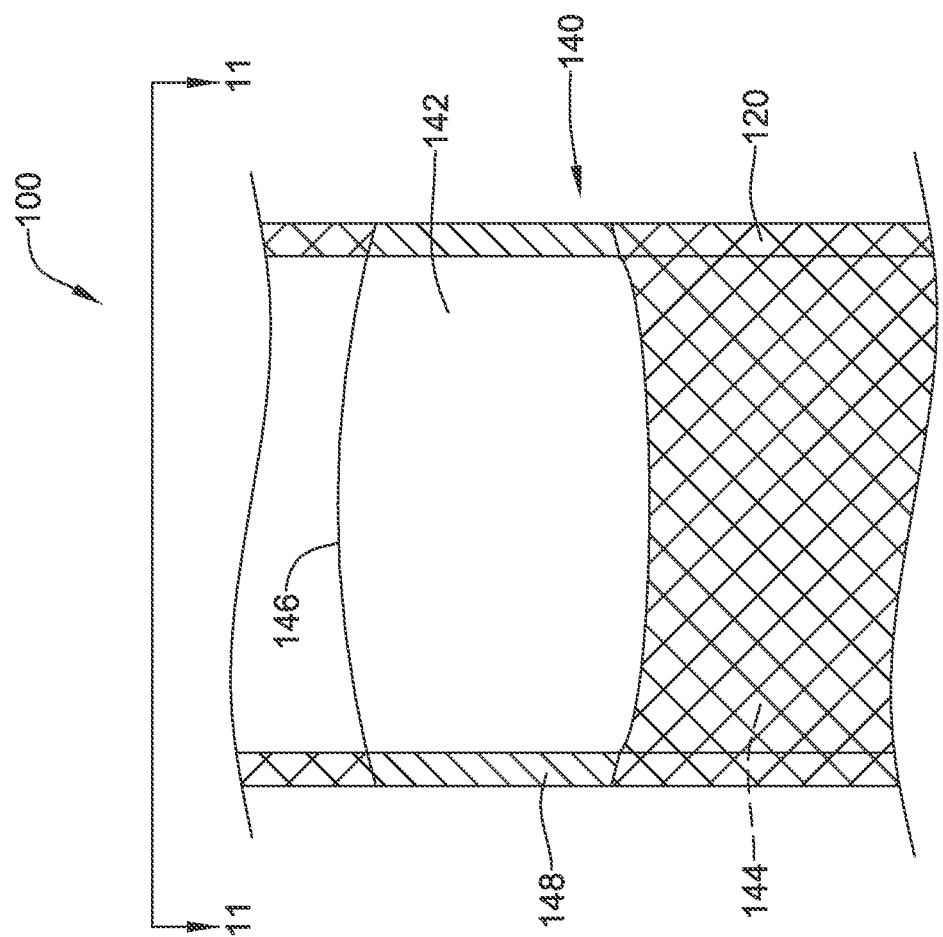

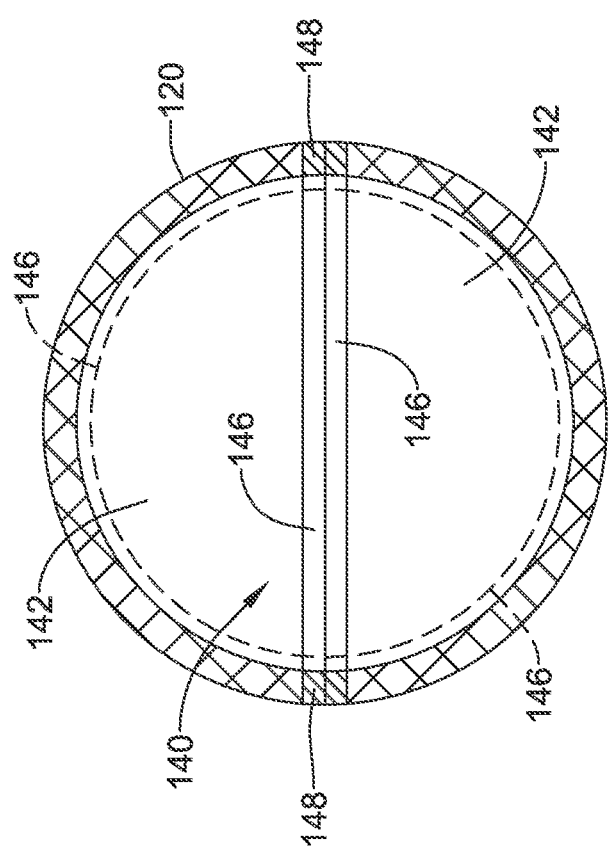

HEART VALVE REMODELING DEVICE

CROSS-REFERENCE TO RELATED APPLICATIONS

This application claims the benefit of priority under 35 U.S.C. § 119 to U.S. Provisional Application Ser. No. 62/428,734, filed Dec. 1, 2016, the entirety of which is incorporated herein by reference.

TECHNICAL FIELD

The present disclosure pertains to medical devices, and methods for manufacturing and/or using medical devices. More particularly, the present disclosure pertains to a heart valve remodeling device and methods of use and/or manufacture therefor.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and/or using medical devices.

SUMMARY

In a first aspect, a heart valve remodeling device may comprise a delivery device including an inner shaft and an outer shaft slidably disposed over the inner shaft, and a braided stent fixedly attached to the inner shaft at a distal end and fixedly attached to the outer shaft at a proximal end, the braided stent being translatable between an elongated configuration and a deployed configuration. The braided stent may include a valve having two or more leaflets disposed within the braided stent.

In addition or alternatively, and in a second aspect, the inner shaft extends through the valve.

In addition or alternatively, and in a third aspect, the valve is translatable between a collapsed configuration and an expanded configuration.

In addition or alternatively, and in a fourth aspect, the valve translates between the collapsed configuration and the expanded configuration as the braided stent translates between the elongated configuration and the deployed configuration, respectively.

In addition or alternatively, and in a fifth aspect, the valve is secured to the braided stent.

In addition or alternatively, and in a sixth aspect, the valve is fixedly secured to the braided stent.

In addition or alternatively, and in a seventh aspect, the valve is bonded to a sealing layer disposed over at least a portion of an outer surface of the braided stent.

In addition or alternatively, and in an eighth aspect, free edges of the two or more leaflets are configured to contact each other and the inner shaft in a closed configuration during diastole and the free edges of the two or more leaflets are configured to spread apart in an open configuration during systole.

In addition or alternatively, and in a ninth aspect, the valve is formed of a polymer material.

In addition or alternatively, and in a tenth aspect, the valve includes an upstream cylindrical portion integrally formed with each of the two or more leaflets.

In addition or alternatively, and in an eleventh aspect, the upstream cylindrical portion is disposed within the braided stent.

In addition or alternatively, and in a twelfth aspect, in the deployed configuration, the braided stent defines a generally cylindrical central portion, a tapered proximal portion extending proximally from the central portion, and a tapered distal portion extending distally from the central portion.

In addition or alternatively, and in a thirteenth aspect, in the deployed configuration, a central portion of the braided stent has a greater outer extent than the proximal end of the braided stent and the distal end of the braided stent.

In addition or alternatively, and in a fourteenth aspect, the valve is disposed within the central portion of the braided stent.

In addition or alternatively, and in a fifteenth aspect, a heart valve remodeling device may comprise a delivery device including an inner shaft and an outer shaft slidably disposed over the inner shaft, and a braided stent non-removably secured to the inner shaft and non-removably secured to the outer shaft, the braided stent being translatable between an elongated configuration and a deployed configuration by movement of the inner shaft relative to the outer shaft. The braided stent may include a valve having two or more leaflets disposed within the braided stent, wherein adjacent leaflets of the two or more leaflets form longitudinally-oriented commissures proximate a perimeter of the valve, the commissures being fixedly secured to the braided stent along their length.

In addition or alternatively, and in a sixteenth aspect, in the deployed configuration, the braided stent defines a generally cylindrical central portion, a tapered upstream portion extending from the central portion, and a tapered downstream portion extending from the central portion.

In addition or alternatively, and in a seventeenth aspect, the valve includes an upstream cylindrical portion integrally formed with each of the two or more leaflets, the two or more leaflets extending downstream from the cylindrical portion.

In addition or alternatively, and in an eighteenth aspect, the upstream cylindrical portion is fixedly attached to the braided stent.

In addition or alternatively, and in a nineteenth aspect, the commissures are embedded into the braided stent.

In addition or alternatively, and in a twentieth aspect, a heart valve remodeling device may comprise an elongate guidewire, an inner shaft slidably disposed over the guidewire, an outer shaft slidably disposed over the inner shaft, wherein the inner shaft extends distally of the outer shaft, a braided wire frame configured to shift between an elongated delivery configuration and a deployed configuration as a result of relative longitudinal movement between the inner shaft and the outer shaft, the braided wire frame being fixedly attached to the inner shaft and the outer shaft, and a polymer valve structure comprising a hollow cylindrical body and two or more leaflets integrally formed with the cylindrical body, the polymer valve structure being disposed within the braided wire frame with the two or more leaflets being radially spaced apart from the braided wire frame when the braided wire frame is in the deployed configuration and the leaflets are in a closed configuration.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which:

FIG. 5 an example heart valve remodeling device disposed in a native heart valve in the deployed configuration;

FIGS. 6-7 illustrate an example manufacturing process for an example heart valve remodeling device;

FIG. 8 is a partial cut-away view of an example heart valve remodeling device;

FIG. 9A is a top view of one embodiment of the example heart valve remodeling device of FIG. 8;

FIG. 9B is a top view of an alternate embodiment of the example heart valve remodeling device of FIG. 8;

FIG. 10 is a partial cut-away view of an example heart valve remodeling device; and FIG. 11 is a top view of the example heart valve remodeling device of FIG. 10.

Figure 1:
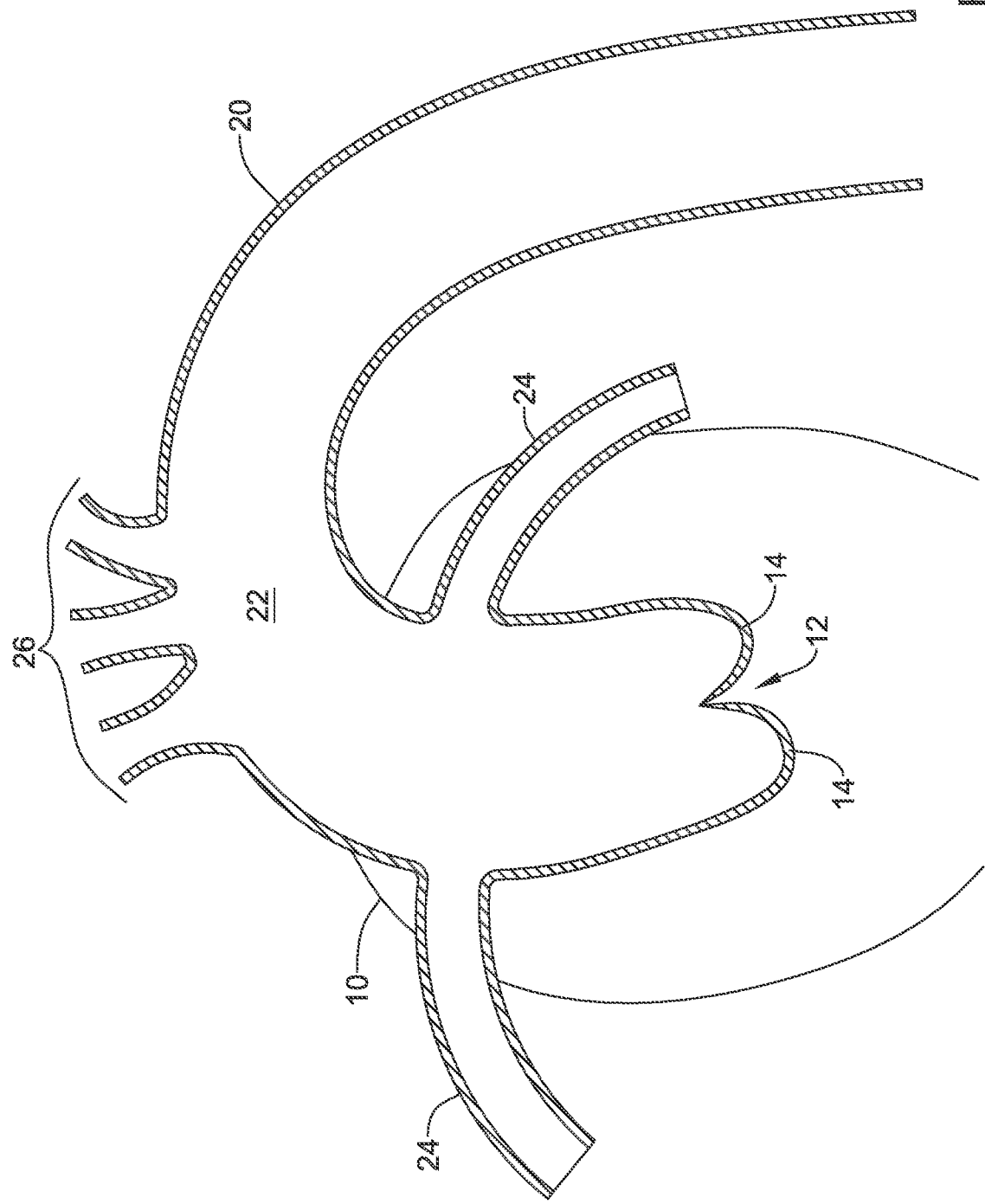
FIG. 1 is a schematic partial cut-away view of elements of an example heart and certain connected vasculature.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The terms "transaortic valve implantation" and "transcatheter aortic valve implantation" may be used interchangeably, and may each be referred to using the acronym "TAVI". The terms "transaortic valve replacement" and "transcatheter aortic valve replacement" may be used interchangeably, and may each be referred to using the acronym "TAVR".

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some mammalian hearts (e.g., human, etc.) include four heart valves: a tricuspid valve, a pulmonary valve, an aortic valve, and a mitral valve. Some relatively common medical conditions may include or be the result of inefficiency, ineffectiveness, or complete failure of one or more of the valves within the heart. Treatment of defective heart valves poses other challenges in that the treatment often requires the repair or outright replacement of the defective valve. Such therapies may be highly invasive to the patient. Disclosed herein are medical devices that may be used within a portion of the cardiovascular system in order to diagnose, treat, and/or repair the system, for example during and/or in conjunction with a TAVI or TAVR procedure, or in place of a TAVI or TAVR procedure in patients not suitable for such. At least some of the medical devices disclosed herein may be delivered percutaneously and, thus, may be much less invasive to the patient, although other surgical methods and approaches may also be used. The devices disclosed herein may also provide a number of additional desirable features and benefits as described in more detail below. For the purpose of this disclosure, the discussion below is directed toward the treatment of a native aortic valve and will be so described in the interest of brevity. This, however, is not intended to be limiting as the skilled person will recognize that the following discussion may also apply to a mitral valve or another heart valve with no or minimal changes to the structure and/or scope of the disclosure. Similarly, the medical devices disclosed herein may have applications and uses in other portions of a patient's anatomy, such as but not limited to, arteries, veins, and/or other body lumens.

FIG. 1 illustrates a schematic partial cut-away view of a portion of a patient's heart 10 including the aortic valve 12 having valve leaflets 14, and certain connected vasculature, such as the aorta 20 connected to the aortic valve 12 of the heart 10 by the aortic arch 22, the coronary arteries 24, and other large arteries 26 (e.g., subclavian arteries, carotid arteries, brachiocephalic artery) that extend from the aortic arch 22 to important internal organs. As mentioned above, for the purpose of this disclosure, the discussion below is directed toward use in the aortic valve 12 and will be so described in the interest of brevity. This, however, is not intended to be limiting as the skilled person will recognize that the following discussion may also apply to other heart valves, vessels, and/or treatment locations within a patient with no or minimal changes to the structure and/or scope of the disclosure.

When providing treatment to a native heart valve, the native heart valve and/or the leaflets thereof may sometimes be calcified and/or subject to stenosis, which may cause and/or aggravate certain conditions. It may be beneficial, for example when a replacement heart valve implant is prescribed, to remodel the native heart valve anatomy prior to performing the procedure (e.g., TAVI, TAVR, etc.) in order to prepare the native heart valve anatomy to receive the replacement heart valve implant. One such way to remodel a native aortic valve is via a balloon aortic valvuloplasty (BAV) procedure. However, expansion of a balloon within the native aortic valve restricts blood flow through the native aortic valve. Often, such a procedure is accompanied by "rapid pacing" of the heart in order to prevent the pressure differential within the heart and/or on opposite sides of the native aortic valve from causing damage to the heart and/or other anatomy. However, "rapid pacing" of the heart does carry certain risks and could cause other damage to the patient. Disclosed herein are devices capable of taking the place of previous BAV devices for remodeling the native aortic valve without the need for "rapid pacing" of the heart. Additionally, the disclosed devices may permit a patient to be held in a stable condition for a longer period of time while the device is in an expanded configuration during the remodeling process. A longer period of time in the expanded configuration may provide better remodeling results and result a more stable platform for installation of the replacement heart valve implant.

Figure 2:
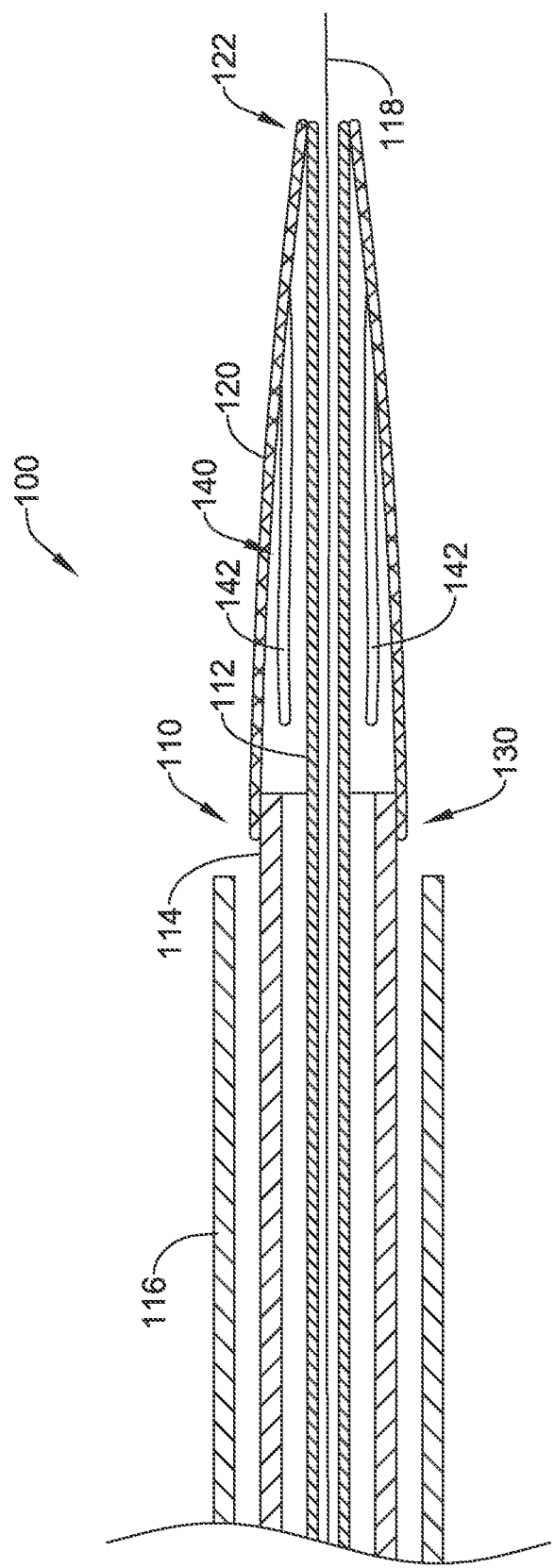
FIG. 2 illustrates an example heart valve remodeling device in an elongated configuration.

FIG. 2 illustrates a heart valve remodeling device 100 in an elongated delivery configuration. The heart valve remodeling device 100 may comprise a delivery device 110 including an inner shaft 112 and an outer shaft 114 slidably disposed over the inner shaft 112. A distal end of the inner shaft 112 may extend distally of a distal end of the outer shaft 114. In some embodiments, the heart valve remodeling device 100 and/or the delivery device 110 may further include a delivery sheath 116 having a lumen extending from a proximal end to a distal end, the lumen being configured to slidably receive the outer shaft 114 and the inner shaft 112. In some embodiments, the delivery sheath 116 may also be used in one or more additional procedures or interventions, for example in a TAVI or TAVR procedure. In some embodiments, the heart valve remodeling device 100 may include an elongate guidewire 118 slidably disposed within a lumen of the inner shaft 112. In other words, the inner shaft 112 may be slidably disposed over the elongate guidewire 118. In some embodiments, the elongate guidewire 118 may also be used in one or more additional procedures or interventions, for example in a TAVI or TAVR procedure. Some examples of suitable but non-limiting materials for the inner shaft 112, the outer shaft 114, the delivery sheath 116, and/or the elongate guidewire 118 are described below.

The heart valve remodeling device 100 may include a braided wire frame or stent 120 fixedly attached and/or non-removably secured to the inner shaft 112 at an upstream or distal end 122 of the braided wire frame or stent 120 and fixedly attached and/or non-removably secured to the outer shaft 114 at a downstream or proximal end 130 of the braided wire frame or stent 120. The braided wire frame or stent 120 may be translatable between an elongated delivery configuration, and a deployed configuration by movement of the inner shaft 112 relative to the outer shaft 114 and/or as a result of relative longitudinal movement between the inner shaft 112 and the outer shaft 114. The braided wire frame or stent 120 and/or the heart valve remodeling device 100 may include a valve and/or a polymer valve structure 140 having two or more leaflets 142 disposed within the braided wire frame or stent 120. The valve and/or polymer valve structure 140 may be translatable between a collapsed configuration and an expanded configuration, as will be described in more detail below. Some examples of suitable but non-limiting materials for the braided wire frame or stent 120 and/or the valve and/or polymer valve structure 140 are described below.

Figure 3:
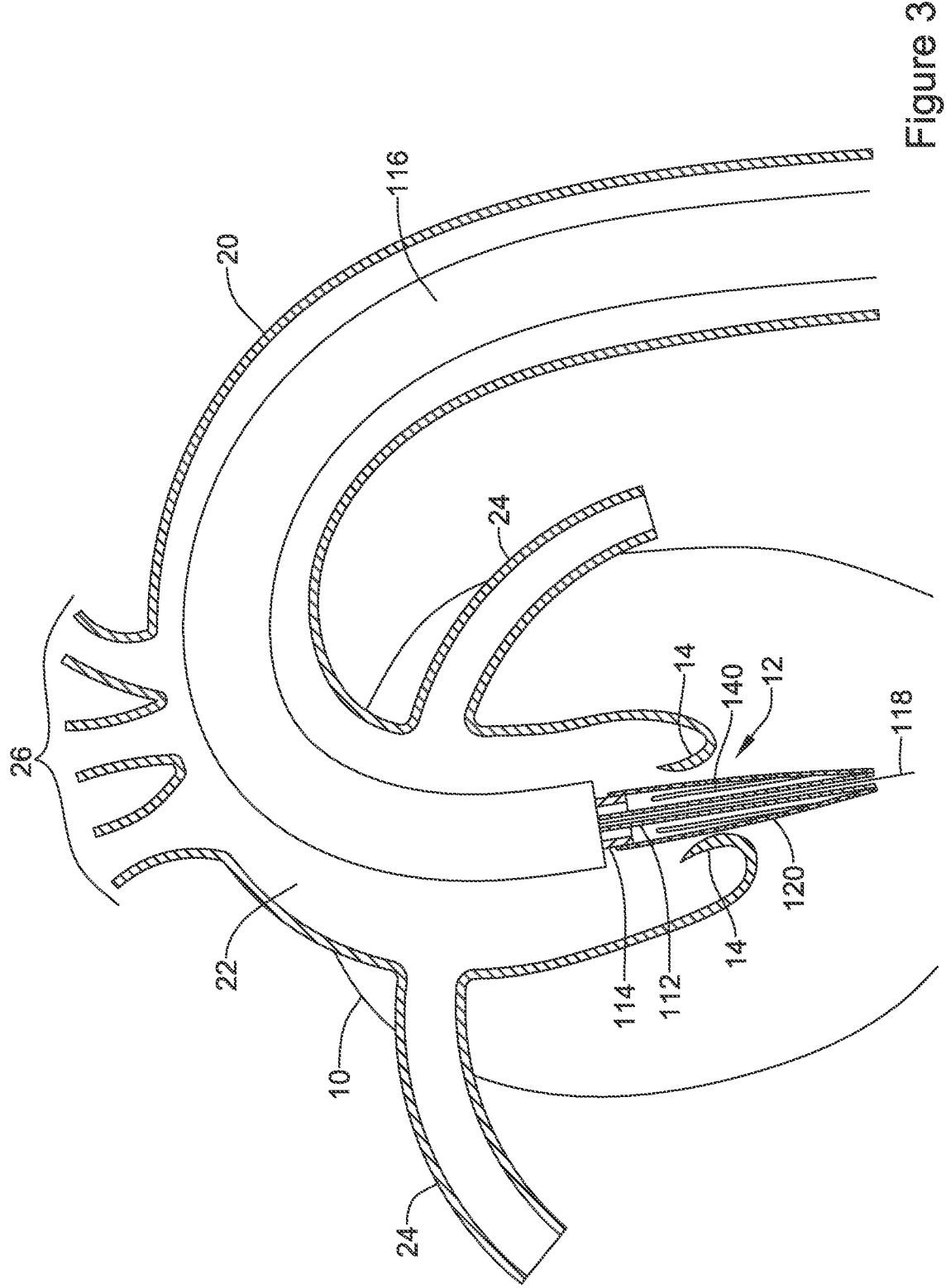
FIG. 3 illustrates an example heart valve remodeling device disposed in a native heart valve in the elongated configuration.

As shown in FIG. 3, the delivery device 110 (not shown) and/or the delivery sheath 116 may be advanced over the elongate guidewire 118 to a heart valve (e.g., the aortic valve 12, the mitral valve, etc.) or another suitable treatment site with the braided wire frame or stent 120 in the elongated delivery configuration and the valve or polymer valve structure 140 disposed therein in the collapsed configuration. The braided wire frame or stent 120 may be positioned between the native valve leaflets 14 and/or within the annulus of the native aortic valve 12. The inner shaft 112 may extend through the valve or polymer valve structure 140. The valve or polymer valve structure 140 may be secured and/or attached to the braided wire frame or stent 120. In some embodiments, the valve or polymer valve structure 140 may be fixedly secured and/or fixedly attached to the braided wire frame or stent 120. The use of a braided wire frame or stent 120 instead of a polymeric balloon, as in previous BAV devices, permits the use of fluoroscopy or other imaging techniques to track and/or identify positioning of the heart valve remodeling device 100 without using contrast media, CT scanning, echocardiography, or where such imaging is unavailable or of poor quality. After positioning the braided wire frame or stent 120 within the annulus of the native aortic valve 12, the braided wire frame or stent 120 may be translated from the elongated delivery configuration to the deployed configuration, as seen in FIGS. 4 and 5 for example.

Figure 4:
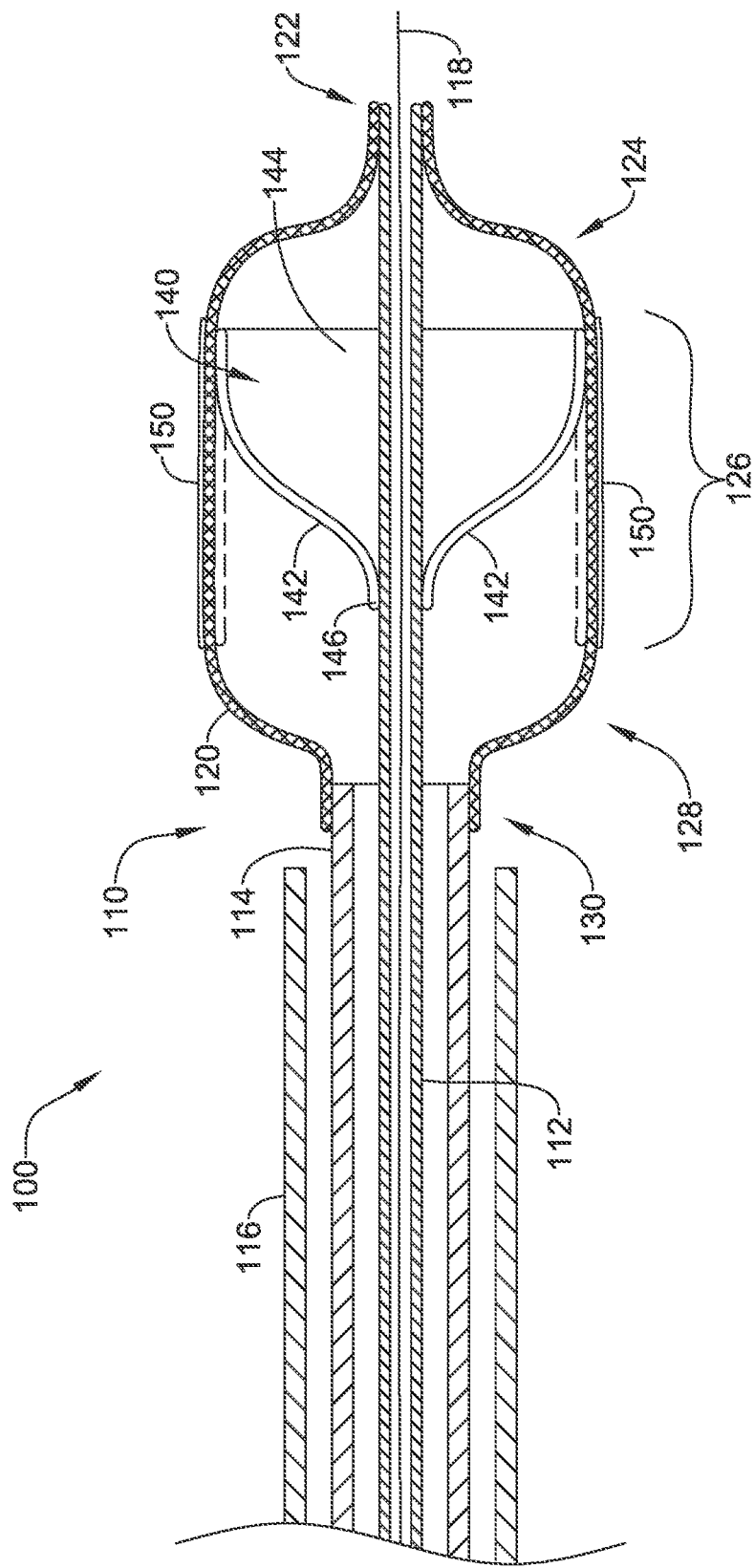
FIG. 4 illustrates an example heart valve remodeling device in a deployed configuration.

FIGS. 4 and 5 show the heart valve remodeling device 100 in an expanded deployed configuration. In the deployed configuration, the braided wire frame or stent 120 may define a generally cylindrical central portion 126, a tapered downstream or proximal portion 128, and a tapered upstream or distal portion 124. The tapered downstream or proximal portion 128 may extend proximally from the generally cylindrical central portion 126 and taper radially inwardly toward the proximal end 130. The tapered upstream or distal portion 124 may extend distally from the generally cylindrical central portion 126 and taper radially inwardly toward the distal end 122. In the deployed configuration, the generally cylindrical central portion 126 of the braided wire frame or stent 120 may have a greater outer extent than the proximal end 130 of the braided wire frame or stent 120. In the deployed configuration, the generally cylindrical central portion 126 of the braided wire frame or stent 120 may have a greater outer extent than the distal end 122 of the braided wire frame or stent 120. For example, the proximal end 130 of the braided wire frame or stent 120 may have a greater outer extent than the distal end 122 of the braided wire frame or stent 120 in the elongated delivery configuration and/or the deployed configuration.

The valve or polymer valve structure 140 may include two or more leaflets 142 disposed within the braided wire frame or stent 120. The valve or polymer valve structure 140 may be translatable between a collapsed configuration and an expanded configuration. The valve or polymer valve structure 140 may translate between the collapsed configuration and the expanded configuration as the braided wire frame or stent 120 translates between the elongated delivery configuration and the deployed configuration, respectively. The valve or polymer valve structure 140 may include an upstream cylindrical portion 144 integrally formed with each of the two or more leaflets 142 as a single unitary structure. The two or more leaflets 142 may each extend downstream from the upstream cylindrical portion 144. Described another way, the valve or polymer valve structure 140 may comprise a hollow cylindrical body 144 and two or more leaflets 142 integrally formed with the hollow cylindrical body 144. The valve or polymer valve structure 140 may be disposed within the generally cylindrical central portion 126 of the braided wire frame or stent 120. The upstream cylindrical portion or hollow cylindrical body 144 may be disposed within and/or fixedly attached to the braided wire frame or stent 120. In at least some embodiments, the upstream cylindrical portion or hollow cylindrical body 144 may be disposed within and/or fixedly attached to the generally cylindrical central portion 126 of the braided wire frame or stent 120. In some embodiments, the valve or polymer valve structure 140 may be bonded to a sealing layer 150 disposed over at least a portion of an outer surface of the braided wire frame or stent 120. Generally speaking, the sealing layer 150 may be positioned and/or disposed on the at least a portion of the outer surface of the braided wire frame or stent 120 so as not to obstruct and/or impede fluid/blood flow through the valve or polymer valve structure 140 and/or the heart valve remodeling device 100 when the heart valve remodeling device 100 is disposed within the annulus of the native aortic valve 12 in the deployed configuration.

When the valve or polymer valve structure 140 is disposed within the annulus of the native aortic valve 12 in the expanded configuration (within the braided wire frame or stent 120 in the deployed configuration), free edges 146 of the two or more leaflets 142 may be configured to contact each other and the inner shaft 112 in a closed configuration during diastole, and the free edges 146 of the two or more leaflets 142 may be configured to spread apart in an open configuration (as shown in phantom in FIG. 4, for example) during systole.

As shown in FIG. 5, after positioning the braided wire frame or stent 120 within the annulus of the native heart valve (e.g., aortic valve 12, etc.), the braided wire frame or stent 120 may be translated from the elongated delivery configuration to the deployed configuration. As discussed above, the heart valve remodeling device 100 may be held in place within the patient over time without the need for rapid pacing of the heart and/or without negatively impacting patient stability. The valve or polymer valve structure 140 may function as a temporary heart valve to maintain function of the cardiovascular system during remodeling of the native heart valve (e.g., aortic valve 12, etc.). As also seen in FIG. 5, when the braided wire frame or stent 120 is positioned within the native heart valve (e.g., aortic valve 12, etc.), the tapered upstream or distal portion 124 of the braided wire frame or stent 120 may be positioned upstream of the annulus of the native heart valve (e.g., aortic valve 12, etc.) and the tapered downstream or proximal portion 128 of the braided wire frame or stent 120 may be positioned downstream of the annulus of the native heart valve (e.g., aortic valve 12, etc.). The valve or polymer valve structure 140 may functionally take the place of the native valve leaflets 14. Radial outward expansion of the generally cylindrical central portion 126 of the braided wire frame or stent 120 may remodel and/or resize the native heart valve (e.g., aortic valve 12, etc.), for example, to prepare for a TAVI or TAVR procedure.

FIG. 6 schematically illustrates an example mandrel 200 and spray nozzle 210 suitable for making the valve or polymer valve structure 140. The illustrated mandrel 200 is shown in a configuration suitable for forming a bicuspid or two-leaflet valve or polymer valve structure 140. The skilled artisan will recognize that other alternative configurations, for example a tricuspid or three-leaflet valve, or other suitable configurations may also be used. Similarly, while the exemplary process is shown using the spray nozzle 210, other means of forming the valve or polymer valve structure 140 may also be used. Additionally, while FIG. 6 illustrates that the mandrel 200 may be rotated and/or translated axially (e.g., reciprocated, etc.), in some embodiments, the spray nozzle 210 may move around and/or translate axially (e.g., reciprocate, etc.) along the mandrel 200. For example, relative movement between the mandrel 200 and the spray nozzle 210 may be used to form the valve or polymer valve structure 140. Other configurations, such as, a series of spray nozzles disposed circumferentially around and/or along a length of the mandrel 200, for example are also contemplated for forming the valve or polymer valve structure 140 on the mandrel 200.

In some embodiments, the valve or polymer valve structure 140 may be formed by dissolving a polymer in suitable solvents and spraying one or more layers of the solution onto the mandrel 200. The solvents can then be removed, for example by being left to evaporate off or being flashed off using an oven, leaving the valve or polymer valve structure 140 formed on the mandrel 200. The thickness of discrete areas of the valve or polymer valve structure 140 may be varied and/or strategically modified by varying the speed of rotation, axial translation, and/or reciprocation and/or implementing pauses in the rotation, axial translation, and/or reciprocation of the mandrel 200 and/or the spray nozzle 210, for example. In some embodiments, the valve or polymer valve structure 140 may then be cut, for example using a blade or a laser, to form the free edges 146 of the two or more leaflets 142.

The valve or polymer valve structure 140 may then be removed from the mandrel 200 and inserted into the braided wire frame or stent 120. In some embodiments, the valve or polymer valve structure 140 may be fixedly secured and/or attached to the braided wire frame or stent 120 with sutures, filaments, wires, staples, or other suitable fixation elements. In some embodiments, the braided wire frame or stent 120 may be loaded over the valve or polymer valve structure 140 formed on the mandrel 200, as shown in FIG. 7 for example. One or more layers of a polymer material may be sprayed over the outside of the valve or polymer valve structure 140 and the braided wire frame or stent 120, so that the valve or polymer valve structure 140 becomes fixedly attached to the braided wire frame or stent 120 when the solvents have been removed. In some embodiments, one or more portions of the braided wire frame or stent 120 may be masked, with a water-soluble masking material for example, to strategically place attachment points between the valve or polymer valve structure 140 and the braided wire frame or stent 120. Similar to above, once the solvents have been removed, the heart valve remodeling device 100, the valve or polymer valve structure 140, and/or the braided wire frame or stent 120 may be rinsed in water to remove the water soluble masking material along with any excess polymer material. In some embodiments, spraying one or more layers of the polymer material over the outside of the valve or polymer valve structure 140 and the braided wire frame or stent 120, in conjunction with or in the absence of the water soluble masking material, may form the sealing layer 150 disposed over at least a portion of the outer surface of the braided wire frame or stent 120. The valve and/or polymer valve structure 140 may be bonded to the sealing layer 150 disposed over at least a portion of the outer surface of the braided wire frame or stent 120.

FIGS. 8-9B illustrate an example configuration for the valve or polymer valve structure 140 within the braided wire frame or stent 120, shown before attachment to and/or being disposed over the inner shaft 112. FIGS. 9A and 9B are cross-sectional views taken at line 9-9 of FIG. 8 illustrating alternative configurations of the disclosed valve or polymer valve structure 140. For ease of understanding, a portion of the braided wire frame or stent 120 has been cut away in FIG. 8 to enable viewing of the valve or polymer valve structure 140 and/or the two or more leaflets 142 disposed within the braided wire frame or stent 120. The free edges 146 of the two or more leaflets 142 may be configured to contact each other (and the inner shaft 112, which is not shown in FIGS. 8-9B) in a closed configuration during diastole, and the free edges 146 of the two or more leaflets 142 may be configured to spread apart in an open configuration (as shown in phantom in FIGS. 9A and 9B, for example) during systole. In some embodiments, the two or more leaflets 142 may be radially spaced apart from the braided wire frame or stent 120 when the braided wire frame or stent 120 is in the deployed configuration and the two or more leaflets 142 are in the closed configuration.

In some embodiments of the configuration shown in FIGS. 8-9B, longitudinally-oriented valve commissures 148 formed by adjacent leaflets 142 of the two or more leaflets 142 may be free standing and unsupported, except for the valve or polymer valve structure 140 itself. In some embodiments, unsupported longitudinally-oriented valve commissures 148 may be configured to invert during diastole. In some embodiments, the valve or polymer valve structure 140 having unsupported longitudinally-oriented valve commissures 148 may have a smaller opening through the valve or polymer valve structure 140 during systole (e.g., in the open configuration) than configurations having supported longitudinally-oriented valve commissures 148 (described further below). For example, in some embodiments, the opening through the valve or polymer valve structure 140 between the free edges 146 of the two or more leaflets 142 in the open configuration, as seen in phantom in FIG. 9B, may be smaller than that shown in phantom in the configuration of FIG. 9A. In some embodiments, the two or more leaflets 142 may be radially spaced apart from the braided wire frame or stent 120 when the braided wire frame or stent 120 is in the deployed configuration and the two or more leaflets 142 are in the open configuration, as seen in FIG. 9B for example. The size of the opening and/or the configuration of the two or more leaflets 142 may be selected and/or varied depending upon the desired use, conditions, placement, etc. of the valve or polymer valve structure 140. In some embodiments, use in a body lumen or situation other than the native heart valve described above, or in patients with special circumstances for example, may have differing flow requirements, etc.

FIGS. 10 and 11 illustrate an example configuration for the valve or polymer valve structure 140 within the braided wire frame or stent 120, shown before attachment to and/or being disposed over the inner shaft 112. For ease of understanding, a portion of the braided wire frame or stent 120 has been cut away in FIG. 10 to enable viewing of the valve or polymer valve structure 140 and/or the two or more leaflets 142 disposed within the braided wire frame or stent 120. The free edges 146 of the two or more leaflets 142 may be configured to contact each other (and the inner shaft 112, which is not shown in FIGS. 10 and 11) in a closed configuration during diastole, and the free edges 146 of the two or more leaflets 142 may be configured to spread apart in an open configuration (as shown in phantom in FIG. 11, for example) during systole.

In some embodiments of the configuration shown in FIGS. 10 and 11, longitudinally-oriented valve commissures 148 formed by adjacent leaflets 142 of the two or more leaflets 142 may be supported by (e.g., attached to, etc.) and/or embedded into the braided wire frame or stent 120. The longitudinally-oriented valve commissures 148 may be formed and/or disposed proximate the perimeter of the valve or polymer valve structure 140 and/or the braided wire frame or stent 120. The longitudinally-oriented valve commissures 148 may be fixedly secured and/or attached directly to, and/or may be embedded into, the braided wire frame or stent 120 along their length and/or the length of the upstream cylindrical portion 144, as seen in FIG. 10 for example. In some embodiments, supported longitudinally-oriented valve commissures 148 may be prevented from inverting during diastole. In some embodiments, the valve or polymer valve structure 140 having supported longitudinally-oriented valve commissures 148 may have a full opening through the valve or polymer valve structure 140 during systole. In other words, in some embodiments, the free edges 146 of the two or more leaflets 142 in the open configuration, as seen in phantom in FIG. 11 for example, may be proximate and/or adjacent to a perimeter of the valve or polymer valve structure 140 and/or the braided wire frame or stent 120.

The materials that can be used for the various components of the heart valve remodeling device 100, the delivery device 110, the braided wire frame or stent 120, the valve or polymer valve structure 140, and/or the sealing layer 150, etc. (and/or other systems or components disclosed herein) and the various elements thereof disclosed herein may include those commonly associated with medical devices. For simplicity purposes, the following discussion makes reference to the heart valve remodeling device 100, the delivery device 110, the braided wire frame or stent 120, the valve or polymer valve structure 140, and/or the sealing layer 150, etc. However, this is not intended to limit the devices and methods described herein, as the discussion may be applied to other elements, members, components, or devices disclosed herein, such as, but not limited to, the inner shaft 112, the outer shaft 114, the delivery sheath 116, the elongate guidewire 118, the two or more leaflets 142, the upstream cylindrical portion 144, etc. and/or elements or components thereof.

In some embodiments, the heart valve remodeling device 100, the delivery device 110, the inner shaft 112, the outer shaft 114, the delivery sheath 116, the elongate guidewire 118, the braided wire frame or stent 120, etc., and/or components thereof, may be made from a metal, metal alloy, a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the heart valve remodeling device 100, the delivery device 110, the braided wire frame or stent 120, the valve or polymer valve structure 140, and/or the sealing layer 150, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the heart valve remodeling device 100, the delivery device 110, the braided wire frame or stent 120, the valve or polymer valve structure 140, and/or the sealing layer 150, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the heart valve remodeling device 100, the delivery device 110, the braided wire frame or stent 120, the valve or polymer valve structure 140, and/or the sealing layer 150, etc. to achieve the same result.

In some embodiments, a degree of Magnetic Resonance Imaging (MM) compatibility is imparted into the heart valve remodeling device 100, the delivery device 110, the braided wire frame or stent 120, the valve or polymer valve structure 140, and/or the sealing layer 150, etc. For example, the heart valve remodeling device 100, the delivery device 110, the braided wire frame or stent 120, the valve or polymer valve structure 140, and/or the sealing layer 150, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The heart valve remodeling device 100, the delivery device 110, the braided wire frame or stent 120, the valve or polymer valve structure 140, and/or the sealing layer 150, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the heart valve remodeling device 100, the delivery device 110, the braided wire frame or stent 120, the valve or polymer valve structure 140, the two or more leaflets 142, the upstream cylindrical portion 144, the commissures 148, and/or the sealing layer 150, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A heart valve remodeling device, comprising:
a delivery device including an inner shaft and an outer shaft slidably disposed over the inner shaft; and
a braided stent non-removably secured to the inner shaft at a distal end and non-removably secured to the outer shaft at a proximal end, the braided stent being translatable between an elongated configuration and a deployed configuration as a result of relative movement between the inner shaft and the outer shaft;
wherein the braided stent includes a polymer valve having two or more leaflets disposed within the braided stent, wherein adjacent leaflets of the two or more leaflets form longitudinally-oriented commissures proximate a perimeter of the valve, the commissures being fixedly attached to the braided stent along their length.

2. The heart valve remodeling device of claim 1, wherein the inner shaft extends through the valve.

3. The heart valve remodeling device of claim 1, wherein the valve is translatable between a collapsed configuration and an expanded configuration.

4. The heart valve remodeling device of claim 3, wherein the valve translates between the collapsed configuration and the expanded configuration as the braided stent translates between the elongated configuration and the deployed configuration, respectively.

5. The heart valve remodeling device of claim 1, wherein the valve is secured to the braided stent.

6. The heart valve remodeling device of claim 5, wherein the valve is fixedly secured to the braided stent.

7. The heart valve remodeling device of claim 6, wherein the valve is bonded to a sealing layer disposed over at least a portion of an outer surface of the braided stent.

8. The heart valve remodeling device of claim 1, wherein free edges of the two or more leaflets are configured to contact each other and the inner shaft in a closed configuration during diastole and the free edges of the two or more leaflets are configured to spread apart in an open configuration during systole.

9. The heart valve remodeling device of claim 1, wherein the valve includes an upstream cylindrical portion integrally formed with each of the two or more leaflets.

10. The heart valve remodeling device of claim 9, wherein the upstream cylindrical portion is disposed within the braided stent.

11. The heart valve remodeling device of claim 1, wherein in the deployed configuration, the braided stent defines a generally cylindrical central portion, a tapered proximal portion extending proximally from the central portion, and a tapered distal portion extending distally from the central portion.

12. The heart valve remodeling device of claim 11, wherein in the deployed configuration, a central portion of the braided stent has a greater outer extent than the proximal end of the braided stent and the distal end of the braided stent.

13. The heart valve remodeling device of claim 11, wherein the valve is disposed within the central portion of the braided stent.

14. A heart valve remodeling device, comprising:
a delivery device including an inner shaft and an outer shaft slidably disposed over the inner shaft; and
a braided stent non-removably secured to the inner shaft and non-removably secured to the outer shaft, the braided stent being translatable between an elongated configuration and a deployed configuration by movement of the inner shaft relative to the outer shaft;
wherein the braided stent includes a valve having two or more leaflets disposed within the braided stent, wherein adjacent leaflets of the two or more leaflets form longitudinally-oriented commissures proximate a perimeter of the valve, the commissures being fixedly secured to the braided stent along their length.

15. The heart valve remodeling device of claim 14, wherein in the deployed configuration, the braided stent defines a generally cylindrical central portion, a tapered upstream portion extending from the central portion, and a tapered downstream portion extending from the central portion.

16. The heart valve remodeling device of claim 15, wherein the valve includes an upstream cylindrical portion integrally formed with each of the two or more leaflets, the two or more leaflets extending downstream from the cylindrical portion.

17. The heart valve remodeling device of claim 16, wherein the upstream cylindrical portion is fixedly attached to the braided stent.

18. The heart valve remodeling device of claim 14, wherein the commissures are embedded into the braided stent.

* * * * *